United States Patent
Plumptre

(10) Patent No.: US 9,108,007 B2
(45) Date of Patent: Aug. 18, 2015

(54) SPINDLE AND BEARING COMBINATION AND DRUG DELIVERY DEVICE

(75) Inventor: David Aubrey Plumptre, Worcestershire (GB)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 1274 days.

(21) Appl. No.: 12/788,755

(22) Filed: May 27, 2010

(65) Prior Publication Data

US 2010/0331786 A1  Dec. 30, 2010

Related U.S. Application Data

(60) Provisional application No. 61/182,861, filed on Jun. 1, 2009.

(30) Foreign Application Priority Data

Jul. 10, 2009  (EP) .................................... 09009046

(51) Int. Cl.
A61M 5/315  (2006.01)
A61M 5/50  (2006.01)

(52) U.S. Cl.
CPC ........... *A61M 5/5066* (2013.01); *A61M 5/3158* (2013.01); *A61M 5/31515* (2013.01); *A61M 5/31511* (2013.01); *A61M 5/5086* (2013.01); *Y10T 29/49826* (2015.01)

(58) Field of Classification Search
CPC ............... A61M 5/31501; A61M 2005/13508; A61M 2005/2073; A61M 5/31511; A61M 5/31515; A61M 5/3158; A61M 5/31581; A61M 5/31583; Y10T 29/49826

USPC ......... 604/134, 135, 155, 207–211, 224, 228, 604/229, 220

See application file for complete search history.

(56) References Cited

U.S. PATENT DOCUMENTS

| 3,302,462 | A |   | 2/1967  | Pursell |
| 4,648,872 | A | * | 3/1987  | Kamen .......................... 604/155 |
| 4,921,486 | A | * | 5/1990  | DeChellis et al. ............. 604/110 |
| 5,084,017 | A | * | 1/1992  | Maffetone ..................... 604/110 |
| 5,423,752 | A |   | 6/1995  | Haber et al. |
| 5,514,097 | A |   | 5/1996  | Knauer |
| 5,584,815 | A |   | 12/1996 | Pawelka et al. |
| 5,591,136 | A |   | 1/1997  | Gabriel |
| 5,792,117 | A |   | 8/1998  | Brown |

(Continued)

FOREIGN PATENT DOCUMENTS

| DE | 93 01 334 U1 | 4/1993 |
| DE | 197 30 999 C1 | 12/1998 |

(Continued)

OTHER PUBLICATIONS

Machine Deisgn, Penton Media, vol. 65, No. 11 (1993) p. 36 "Standard Compression Springs Save Space".

*Primary Examiner* — Nathan R Price
(74) *Attorney, Agent, or Firm* — McDonnell Boehnen Hulbert & Berghoff LLP

(57) ABSTRACT

An improved spindle and bearing combination for a drug delivery device is provided that has a first connection between the spindle and bearing comprising a web and a second connection that replaces the first connection when the web is severed that allows the spindle to rotate relative to the bearing.

9 Claims, 1 Drawing Sheet

(56) References Cited

U.S. PATENT DOCUMENTS

| | | |
|---|---|---|
| 5,820,602 A | 10/1998 | Kovelman et al. |
| 5,921,967 A * | 7/1999 | Sadowski et al. ............ 604/218 |
| 6,090,080 A | 7/2000 | Jost et al. |
| 6,936,032 B1 | 8/2005 | Bush, Jr. et al. |
| 7,951,120 B2 * | 5/2011 | Wolbring et al. ............ 604/220 |
| 8,118,788 B2 * | 2/2012 | Frezza ......................... 604/200 |
| 2003/0187400 A1* | 10/2003 | Liao .............................. 604/195 |
| 2004/0127858 A1 | 7/2004 | Bendek et al. |
| 2004/0162528 A1 | 8/2004 | Horvath et al. |
| 2004/0186437 A1 | 9/2004 | Frenette et al. |
| 2004/0210199 A1 | 10/2004 | Atterbury et al. |
| 2004/0236285 A1 | 11/2004 | Fisher et al. |
| 2004/0254539 A1* | 12/2004 | Wolbring et al. ............ 604/187 |
| 2005/0137571 A1 | 6/2005 | Hommann |
| 2006/0153693 A1 | 7/2006 | Fiechter et al. |
| 2006/0258988 A1 | 11/2006 | Keitel et al. |
| 2007/0005020 A1* | 1/2007 | Laveault ....................... 604/191 |
| 2007/0021718 A1 | 1/2007 | Burren et al. |
| 2008/0027397 A1 | 1/2008 | DeRuntz et al. |
| 2008/0077095 A1 | 3/2008 | Kirchhofer |
| 2008/0208123 A1 | 8/2008 | Hommann |
| 2009/0227959 A1 | 9/2009 | Hirschel et al. |

FOREIGN PATENT DOCUMENTS

| | | |
|---|---|---|
| DE | 298 18 721 U1 | 3/2000 |
| DE | 10 2005 063 311 A1 | 8/2006 |
| DE | 10 2005 060 928 A1 | 6/2007 |
| DE | 10 2006 038 123 A1 | 2/2008 |
| DE | 10 2007 026 083 A1 | 11/2008 |
| EP | 0 897 728 A1 | 2/1999 |
| EP | 0 937 471 A2 | 8/1999 |
| EP | 0 937 472 A2 | 8/1999 |
| EP | 1 541 185 A1 | 6/2005 |
| EP | 1 776 975 A2 | 4/2007 |
| EP | 1 923 084 A1 | 5/2008 |
| GB | 2 443 390 A | 5/2008 |
| WO | 92/18180 A1 | 10/1992 |
| WO | 93/07922 A1 | 4/1993 |
| WO | 96/23973 A1 | 8/1996 |
| WO | 96/39214 A1 | 12/1996 |
| WO | 97/10864 A1 | 3/1997 |
| WO | 99/03520 A1 | 1/1999 |
| WO | 01/19434 A1 | 3/2001 |
| WO | 03/080160 A1 | 10/2003 |
| WO | 2004/020028 A1 | 3/2004 |
| WO | 2004/064902 A1 | 8/2004 |
| WO | 2004/078241 A1 | 9/2004 |
| WO | 2004/078242 A2 | 9/2004 |
| WO | 2004/078293 A1 | 9/2004 |
| WO | 2005/018721 A1 | 3/2005 |
| WO | 2005/044346 A2 | 5/2005 |
| WO | 2005/021072 A1 | 10/2005 |
| WO | 2005/123159 A2 | 12/2005 |
| WO | 2006/024461 A1 | 3/2006 |
| WO | 2006/058883 A2 | 6/2006 |
| WO | 2006/079481 A1 | 8/2006 |
| WO | 2006/089767 A1 | 8/2006 |
| WO | 2006/114395 A1 | 11/2006 |
| WO | 2006/125328 A1 | 11/2006 |
| WO | 2007/017052 A1 | 2/2007 |
| WO | 2007/067889 A1 | 6/2007 |
| WO | 2008/031235 A1 | 3/2008 |
| WO | 2008/074897 A1 | 6/2008 |
| WO | 2008/116766 A1 | 10/2008 |
| WO | 2008/128373 A1 | 10/2008 |

* cited by examiner

SPINDLE AND BEARING COMBINATION AND DRUG DELIVERY DEVICE

THE TECHNICAL FIELD OF THE INVENTION

The present invention relates to a drug delivery device containing an improved spindle used to expel a medicament from a container where the spindle is initially manufactured and assembled into the device having a pressure bearing rigidly attached to its distal end. Before a first dose of medicament is delivered, the pressure bearing is sheared off the spindle causing it to become rotationally connected to the spindle and thus allowing the piston rod to rotate about the bearing surface.

DESCRIPTION OF RELATED ART

Most drug delivery devices use a spindle to advance an elastic (rubber) piston positioned within one end of a container of medicament to cause the medicament to exit the opposite end of the container. In some delivery devices it is necessary to rotate the spindle during dose delivery relative to the rubber piston. To accomplish this movement a bearing plate or disk is positioned at the distal end of the spindle abutting the proximal face of the non-rotatable rubber piston. This bearing plate is typically connected with a universal joint type connection, i.e. one where the spindle can freely rotate and articulate about the center point of the top surface of the plate. As the spindle is rotated and moved in an axial direction the bearing is prevented from rotating because of its engagement with the non-rotatable piston causing both the bearing plate and piston to also move in the axial direction imparting a pressure to the medicament causing it to be expelled from the distal end of the container. Prior to my invention the spindle and bearing were necessarily manufactured as two separate parts, which were then snapped together before being assembled into the drug delivery device. A common example of a drug delivery device is an injection device that contains a multi-dose cartridge. A more specific example would be a pen-type injection device containing a cartridge of insulin that is designed for repeated injections by persons without formal medical training occurs, i.e., patients. This is increasingly common amongst those having diabetes where self-treatment enables such persons to conduct effective management of their diabetes.

Maintaining or reducing the cost of drug delivery devices at reasonable prices is a priority for manufacturers of such devices. One way this can be accomplished is to minimize the number of parts in a device or to improve the assembling steps needed to fabricate the device. My invention achieves both of these cost saving features by providing a spindle and bearing surface that has a first connection between the spindle and disk-shaped bearing that changes to a second connection before a first dose of medicament is delivered to the user. My invention is of greater value when the device is designed as a disposable device rather than reusable device because a disposable device must be as inexpensive as possible to manufacture and easy to dispose of (preferably being suitable for recycling). To meet these requirements the number of parts required for assembly of the device and the number of material types the device is made from need to be kept to a minimum. These and other advantages will become evident from the following more detailed description of the invention.

SUMMARY OF THE INVENTION

The improved spindle and bearing combination of my invention for use in a drug delivery device comprises a rotatable spindle having a distal end and a disk-shaped bearing attached to the distal end through a first connection comprising a web that fixedly attaches the bearing to the spindle to prevent independent movement of the bearing relative to the spindle. In a preferred embodiment the spindle has at least one helical groove positioned longitudinally along the spindle. This first connection is changed to a second connection when the web is severed and disconnected. This second connection is a rotating joint connection, i.e. one where the spindle can freely rotate. Shearing of the web can occur by applying an axial force to the spindle and bearing combination after the combination has been assembled into the drug delivery device. Alternatively, a rotational force can be applied to the bearing plate to shear the web. Either force can be applied by the manufacturer of the device or by the user immediately before or during the delivery of a first dose of medicament.

The term "drug delivery device" according to instant invention shall mean a single-dose or multi-dose, disposable or re-useable device designed to dispense a selected dose of a medicinal product, preferably multiple selected doses, e.g. insulin, growth hormones, low molecular weight heparins, and their analogues and/or derivatives etc. Said device may be of any shape, e.g. compact or pen-type. Dose delivery may be provided through a mechanical (optionally manual) or electrical drive mechanism or stored energy drive mechanism, such as a spring, etc. Dose selection may be provided through a manual mechanism or electronic mechanism. Additionally, said device may contain components designed to monitor physiological properties such as blood glucose levels, etc. Furthermore, the said device may comprise a needle or may be needle-free. In particular, the term "drug delivery device" shall mean a disposable multi-dose pen-type device having mechanical and manual dose delivery and dose selection mechanisms, which is designed for regular use by persons without formal medical training such as patients. Preferably, the drug delivery device is of the injector-type.

The term "engaged" according to instant invention shall particularly mean the interlocking of two or more components of the drive mechanism/drug delivery device, e.g. a spline, thread, or meshed teeth connection, preferably the interlocking of helical grooves or threads of components ("rotationally engaged" or "threadedly engaged").

The term "spindle" according to instant invention shall mean a component adapted to operate through/within the housing, designed to translate axial movement through/within the drug delivery device, preferably from a driver to the piston, for the purpose of discharging/dispensing an injectable product. The spindle may be flexible or not. It may be a simple rod, a lead-screw, a rack and pinion system, a worm gear system, or the like. The spindle shall further mean a component having a circular or non-circular cross-section. It may be made of any suitable material known by a person skilled in the art.

In a preferred embodiment, the spindle comprises at least one, more preferably two, external and/or internal helical grooves or threads. In another preferred embodiment of the spindle, a first helical groove is located at a first end and a second helical groove is located at a second end of the spindle, whereby the said groves may have the same or, preferably, opposite dispositions and may overlap each other. In another preferred embodiment the spindle invention comprises grooves having the same leads at the first and the second end.

In yet another preferred embodiment of instant invention the lead of the first helical groove of the spindle shall be greater than the lead of the second helical groove. More preferred, the ratio of the leads of the helical grooves of the said first and the second helical grooves 1:1.01 to 1:20, even more preferred 1:1.1 to 1:10. Preferably, one of the said grooves is designed to engage a driver to impart either rotation, axial or a combination of rotational and axial movement to the spindle.

The term "first end" according to instant invention shall mean the proximal end. The proximal end of the device or a component of the device shall mean the end, which is closest to the dispensing end of the device.

The term "second end" according to instant invention shall mean the distal end. The distal end of the device or a component of the device shall mean the end, which is furthest away from the dispensing end of the device.

BRIEF DESCRIPTION OF THE DRAWINGS

Without any limitation, the instant invention will be explained in greater detail below in connection with a preferred embodiment and with reference to the drawings in which.

DETAILED DESCRIPTION OF THE EMBODIMENTS

Figure 1:
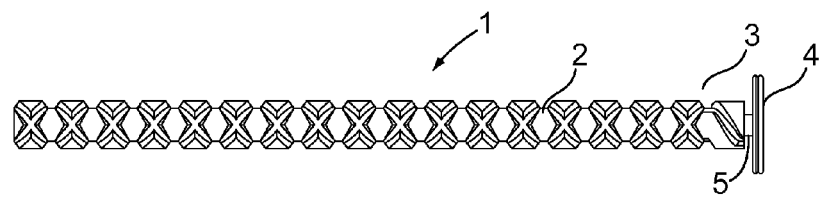
FIG. 1 shows a side view of my invention where the spindle is connected to disk-shaped bearing by a web such that the bearing cannot move independently of the spindle.
Figure 3:
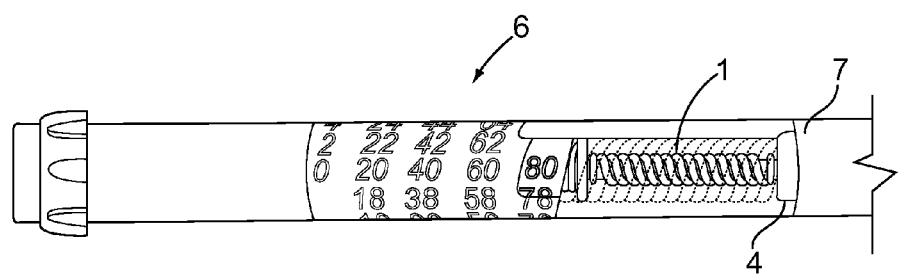
FIG. 3 shows a side cross-sectional view of an example of a drug delivery device where my invention can be used.

Referring first to FIG. 1 there is shown a spindle 1 have two overlapping helical grooves 2 running longitudinally along the spindle having attached to its distal end 3 a disk-shaped bearing 4. Although two helical grooves are depicted a single groove or no groove could also be used. Preferably the combination of the spindle and bearing is fabricated as a single molded part of a polymer material, such as plastic, however, a metal or combination of different materials could be used provided that the material of construction of web 5 can be broken or sheared upon application of a rotational or axial force. The strength or robustness of the web need only be sufficient to allow for the assembly of the combination of the spindle and bearing in a drug delivery device 6 like the representative device shown in FIG. 3 where bearing 4 is abutting piston 7.

Figure 4:
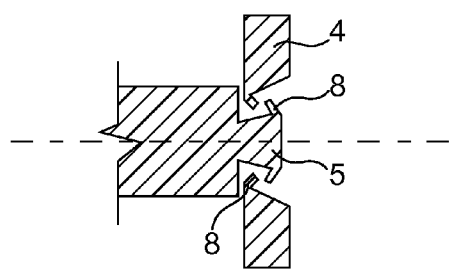
FIG. 4 shows a close up cross-sectional view of the second connection after the web of FIG. 1 is sheared.

Once the combination spindle and bearing of my invention is assembled into the delivery device, the manufacturer or the user will impart a rotational or axial force to the spindle. This will cause the web of the first connection to break allowing the spindle to rotate relative to the stationary bearing thus forming a second rotating joint connection. The web can be of any shape or design as long as it is strong enough to hold the bearing to the distal end of the spindle during assembly of the drug delivery device and is weak enough to shear when a rotational or axial force is applied to the spindle. One preferred web design is where the thickness of the plastic is reduced in a circumferential line at the point where the bearing face and the spindle meet. A rotational or axial force applied to the spindle will be transferred to this circumferential line of thin plastic and will shear the spindle from the proximal face of the bearing. The shape of the distal end of the spindle and the proximal face of the bearing is configured to allow the formation of a rotational connection between the separate parts after the web shear is broken. In a preferred configuration the web is designed such that upon shearing the respective pieces of the web form a type of snap fit or snap lock that holds the bearing to the spindle, yet allows the spindle to rotate with respect to the bearing. A most preferred design is where no pieces are broken off of from the spindle or the bearing that could fall into the device and cause a malfunction. This is illustrated in FIG. 4 where the resulting web shears 8 remain attached to the spindle and bearing. Because the web deforms and stretches during the breaking process, the result is two cooperating pieces 8 that work together retain the bearing on the spindle.

Figure 2:
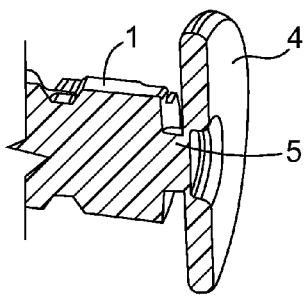
FIG. 2 shows a close up cross-sectional view of the web of FIG. 1.

Although the web that is shown in FIGS. 1, 2 and 4 is an annular ring, it could also take other forms provided that the bearing is free to rotate in the second connection and adequately secured in the first connection.

The foregoing description of the specific embodiments will so fully reveal the general nature of the invention that others can, by applying current knowledge, readily modify and/or adapt for various application such specific embodiments without departing from the generic concept, and therefore such adaptations and modifications are intended to be comprehended within the meaning and range of equivalents of the disclosed embodiments. It is to be understood that the phraseology or terminology herein is for the purpose of description and not of limitation.

The means, materials, and steps for carrying out various disclosed functions may take a variety of alternative forms without departing from the invention. Thus, the expressions "means to . . . " and "means for . . . ", or any method step language as may be found in the specification above or the claims below, followed by a functional statement, are intended to define and cover whatever structural, physical, chemical or electrical element or structure, or whatever method step, which may now or in the future exist which carries out the recited function, whether or not precisely equivalent to the embodiment or embodiments disclosed in the specification above, i.e., other means or steps for carrying out the same function can be used; and it is intended that such expressions be given their broadest interpretation within the terms of the following claims.

The invention claimed is:

1. A spindle and bearing combination for use in a drug delivery device comprising,
 a) a rotatable spindle having a distal end; and
 b) a disk-shaped bearing configured to abut a proximal face of a non-rotatable piston in a medicament container, where the disk-shaped bearing has a first connection and a second connection to the distal end of the spindle, where the first connection comprises a web that fixedly attaches the disk-shaped bearing to the spindle to prevent independent movement of the disk-shaped bearing relative to the spindle and where the second connection is created and replaces the first connection when the web is sheared such that the spindle is rotatably connected to the disk-shaped bearing and the distal end of the spindle is retained within the disk-shaped bearing by a pair of cooperating web shears formed from the sheared web.

2. The spindle and bearing combination of claim 1 where the second connection comprises a joint that allows the spindle to rotate relative to the disk-shaped bearing.

3. The spindle and bearing combination of claim 2 where the second connection prevents accidental separation of the disk-shaped bearing from the spindle.

4. The spindle and bearing combination of claim 1 where the spindle has at least one helical groove positioned longitudinally along the spindle.

5. The spindle and bearing combination of claim 1 where the spindle and disk-shaped bearing are assembled as part of an injection device when the first connection remains intact.

6. The spindle and bearing combination of claim 1 where the spindle and disk-shaped bearing are connected with the second connection during delivery of a first dose with an injection device containing the spindle and bearing combination.

7. The spindle and bearing combination of claim 1 where the spindle and disk-shaped bearing are assembled as part of an injection device and the first connection is modified to the second connection during the assembly of the device.

8. A method of fabricating a spindle and bearing combination for a drug delivery device comprising the steps of,
   a) providing a unitary part comprising,
      i) a rotatable spindle having a distal end and at least one helical groove positioned longitudinally along the spindle; and
      ii) a disk-shaped bearing configured to abut a proximal face of a nonrotatable piston in a medicament container, where the disk-shaped bearing has a first connection comprising a web that fixedly attaches the disk-shaped bearing to the spindle preventing independent movement of the disk-shaped bearing relative to the spindle;
   b) assembling the unitary part into a housing of a drug delivery device; and
   c) shearing the web, thereby deforming and stretching the web, to form a second connection comprising a joint having a pair of cooperating web shears formed from the sheared web that allows the spindle to rotate relative to the disk-shaped bearing and that retains the distal end of the spindle within the disk-shaped bearing.

9. A method of fabricating a secure connection in a drug delivery device comprising the steps of,
   a) providing a unitary part during the assembly of a drug delivery device comprising,
      i) a first portion securely connected to a section portion through a breakable and extendable web; and
   b) assembling the unitary part into a housing of the drug delivery device; and
   c) shearing the web, thereby deforming and stretching the web, to form a second connection comprising a joint having a pair of cooperating web shears formed from the sheared web that allows the first portion to move relative to the second portion while remaining connected to the second portion and that retains the distal end of the spindle within the second portion.

* * * * *